United States Patent [19]
Muranaka et al.

[11] Patent Number: 6,053,059
[45] Date of Patent: *Apr. 25, 2000

[54] ANALYZING SYSTEM OF ORGANIC SUBSTANCE ADHERING TO A SURFACE OF A SAMPLE

[75] Inventors: Seiji Muranaka; Kuniaki Miyake, both of Tokyo, Japan

[73] Assignee: Mitsubishi Denki Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/089,421

[22] Filed: Jun. 3, 1998

[30] Foreign Application Priority Data

Dec. 15, 1997 [JP] Japan ..................... 9-344572

[51] Int. Cl.⁷ ..................................... G01N 1/00
[52] U.S. Cl. ..................... 73/863.12; 73/863.31
[58] Field of Search ............... 73/863.11, 863.12, 73/863.21, 863.31, 863.33, 863.83, 864.71, 864.81, 865.8; 250/288, 288 A

[56] References Cited

U.S. PATENT DOCUMENTS

| | | | |
|---|---|---|---|
| 4,734,579 | 3/1988 | Lucatorto et al. | 250/288 |
| 4,874,946 | 10/1989 | Kazmerski | 250/288 |
| 5,161,417 | 11/1992 | Strong et al. | 73/863.31 |
| 5,201,219 | 4/1993 | Bandurski et al. | 73/863.12 |
| 5,442,175 | 8/1995 | Dawson | 73/863.12 |
| 5,663,561 | 9/1997 | Franzen et al. | 250/288 |

FOREIGN PATENT DOCUMENTS

| | | | |
|---|---|---|---|
| 0013660 | 1/1982 | Japan | 250/288 |
| 7-146220 | 6/1995 | Japan . | |

*Primary Examiner*—Robert Raevis
*Attorney, Agent, or Firm*—McDermott, Will & Emery

[57] ABSTRACT

An organic substance analyzing system identifies and quantifies organic substances adhering to the surface of a sample placed in a chamber for a local organic substance analysis on the surface of the sample. The organic substance analyzing system heats a portion of the sample from the front side or the back side of the sample, collects gases discharged out of the portion of the surface and analyzes the collected gases. A lamp, a laser or an electron beam source is used as a heating means for locally heating a portion to be analyzed on the surface of the sample to locally discharge the gases out of the portion. Otherwise, the entire surface of the sample is heated, and the discharged gases are collected for every section so as to be analyzed.

15 Claims, 5 Drawing Sheets

ANALYZING SYSTEM OF ORGANIC SUBSTANCE ADHERING TO A SURFACE OF A SAMPLE

BACKGROUND OF THE INVENTION

1. Field of the Invention

The present invention relates to an organic substance analyzing system for identifying and quantifying organic substances adhering to the surface of a sample such as a semiconductor wafer.

2. Background Art

Semiconductor devices have been progressively miniaturized in recent years, and it has been realized that the adhesion of organic contaminant substances to the surface of a semiconductor wafer deteriorates the characteristics of the devices heavily, which has not been much of a problem so far. Accordingly, in order to identify the organic substances which deteriorate the device characteristics, it is being requested to establish testing techniques for identifying and quantifying organic substances adhering to the surface of a semiconductor wafer.

Organic substance analyzing methods generally used at present are methods such as GC/MS (Gas Chromatograph Mass Spectroscopy), XPS (X-ray Photoelectron Spectroscopy), FT-IR (Fourier Transform-Infrared Spectroscopy), SIMS (Secondary Ion Mass Spectrometry), NMR (Nuclear Magnetic Resonance), and Contact Angle Measuring Method. Among those methods, the GC/MS has become used most widely with establishment of measuring techniques because of its high detection sensitivity, its high ability to identify the kinds of organic substances and the easiness with which the measurement is made.

FIG. 7 shows a wafer heating unit used in a conventional GC/MS measuring apparatus. A whole surface of a wafer 2 placed in a chamber 1 is heated from the rear side thereof by a heater 3. A carrier gas is supplied through a carrier gas supply pipe 4, and gases discharged out of the heated wafer 2 are collected by a discharged gas collecting means 6 including a discharged gas collecting pipe 5. A discharged gas analyzing means 7 concentrates and separates the collected gases, and analyzes the resultant gases.

As described, the GC/MS method is widely used at present for identifying and quantifying organic substances adhering to the surface of a wafer, thus analyzes the gases discharged when the whole surface of the wafer is heated from its rear side.

In a wafer actually fabricated, however, organic substances adhering to the surface of the wafer are not necessarily uniformly adhered. For example, if a wafer is contaminated by discharged gases of organic substances adhering to a cassette for holding the wafer, more organic substances are adhered in portions in which the wafer is contact with the cassette. Thus, an analyzing techniques for local organic substance has to be established to elucidate the behavior of organic substances locally adhering to a wafer.

With the progress of further miniaturization of the devices, there appears a possibility that organic substances become a main cause for the deterioration of the device characteristics, although up to now the organic substances have been considered to exert less influence on the device characteristics compared with contamination substances such as metals and particles. If, in such a case, the local organic substance analysis is to be performed, a map checking of defective portions becomes possible, and the defect analysis may be performed in more detail and more effectively.

SUMMARY OF THE INVENTION

The present invention has been made to solve the foregoing problems, and it is therefore an object of the present invention to evaluate the distribution of the organic substances adhering to the wafer surface by locally analyzing the organic substances on the specimens and to examine the behavior of organic substances and the local change of the device characteristics.

According to one aspect of the present invention, an organic substance analyzing system is provided for identifying and quantifying organic substances adhering to each portion of a surface of a sample such as a semiconductor wafer. The analyzing system comprises a heating means for heating a portion to be analyzed on the surface of the sample placed in a chamber from the back side of the sample. A means for collecting discharged gas is connected to the chamber for collecting gases discharged out of the sample. A means for analyzing discharged gas is provided for analyzing the discharged gases collected by the discharged gas collecting means.

In the organic substance analyzing system, the heating means may be either a heating light source, a laser light source, or an electron beam irradiating source.

In the organic substance analyzing system, the heating means may be a combination of a heating light source and a light-shielding mask disposed on the back side of the sample and provided with a light-transmitting opening at a position corresponding to a portion of the sample to be analyzed.

According to another aspect of the invention, the analyzing system comprises a heating means for heating a portion to be analyzed on the surface of the sample placed in a chamber from the front side of the sample.

According to another aspect of the invention, the analyzing system comprises a heating means for heating the sample placed in a chamber. A collecting means is provided for collecting gases discharged out of each portion of the sample separately, and the separately collected gases are analyzed for each portion of the sample.

Other and further objects, features and advantages of the invention will appear more fully from the following description

BEST MODE OF CARRYING OUT THE INVENTION

This invention will be described in further detail by way of example with reference to the accompanying drawings.

First Embodiment

Figure 1:
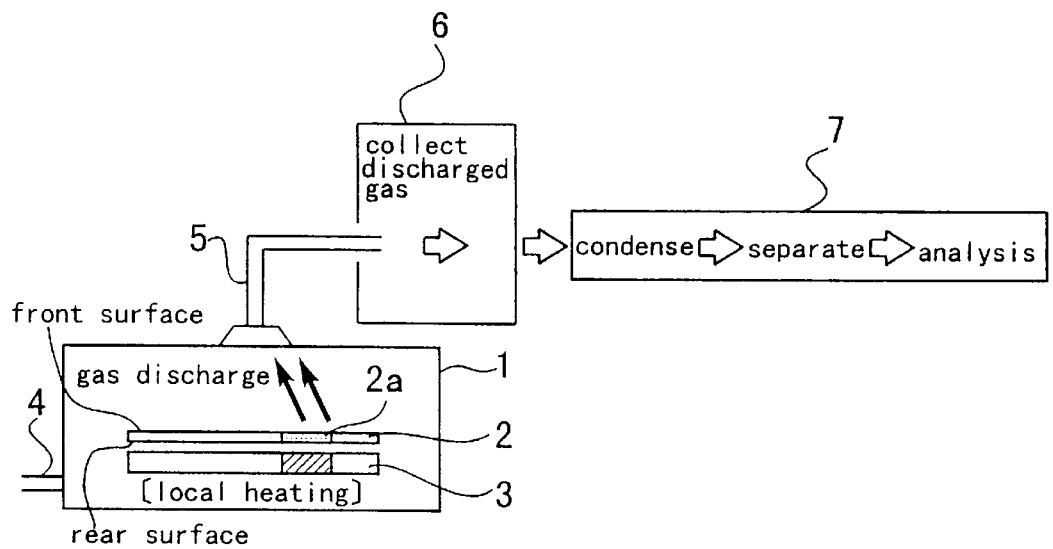
FIG. 1 is a diagram showing a configuration of an organic substance analyzing system in a first embodiment of the present invention for identifying and quantifying organic substances adhering to the surface of a sample or specimen, such as a semiconductor wafer.

FIG. 1 shows an organic substance analyzing system in a first embodiment according to the present invention for identifying and quantifying organic substances adhering to the surface of a sample or specimen, such as a semiconductor wafer. Referring to FIG. 1, there are shown a chamber 1, a wafer 2, i.e., a sample (object of analysis) placed in the chamber 1, a heating device 3 (a heater) for locally heating the wafer 2, a carrier gas supply pipe 4, a discharged gas collecting pipe 5 through which gases discharged out of the wafer 2 are collected, a discharged gas collecting device 6 including the discharged gas collecting pipe 5, and a discharged gas analyzer 7 for analyzing collected gases.

In the apparatus configured above, a portion or region to be subjected to analysis and evaluation (objective region to be analyzed) 2a on the surface of the wafer 2 is heated locally from the back side or rear side thereof by the heating device 3. Then, gases discharged out of the surface of the wafer 2 are analyzed for local analysis of the organic substance.

The gases discharged out of the wafer 2 flow together with a carrier gas through the collecting pipe 5 into the discharged gas collecting device 6, and are collected by the discharged gas collecting device 6. Organic substances contained in the discharged gases thus collected are analyzed by a discharged gas analyzing means 7 for the identification and quantification of the organic substances. Although a GC/MS method is an effective method to be carried out by the discharged gas analyzing device 7, any suitable method other than a GC/MS method may be performed by the discharged gas analyzing device 7.

The wafer 2 is heated at a temperature in the range of 400 to 1000° C. to separate the organic substances from the wafer 2. A heating temperature is varied in accordance with experimental conditions. The experimental conditions are such as boiling points, decomposition temperatures of expected organic substances and a temperature at which the wafer 2 is heated in the subsequent process, and are taken into consideration in determining heating temperature. For example, if the subsequent process is an oxidation process, the wafer 2 is heated at a heating temperature equal to an oxidation temperature. This makes it possible to reproduce the separation phenomena of the organic substances from the wafer 2, and thus a detailed evaluation may be performed. In the following various heating methods to be explained, heating temperatures are also in the range of 400 to 1000° C.

Thus, the above-mentioned apparatus and method make it possible to locally examine the wafer 2 for a local analysis of organic substances adhering to the surface of the wafer 2, and hence it becomes possible to evaluate how the organic substances on the surface of the wafer 2 are distributed.

Second Embodiment

Figure 2:
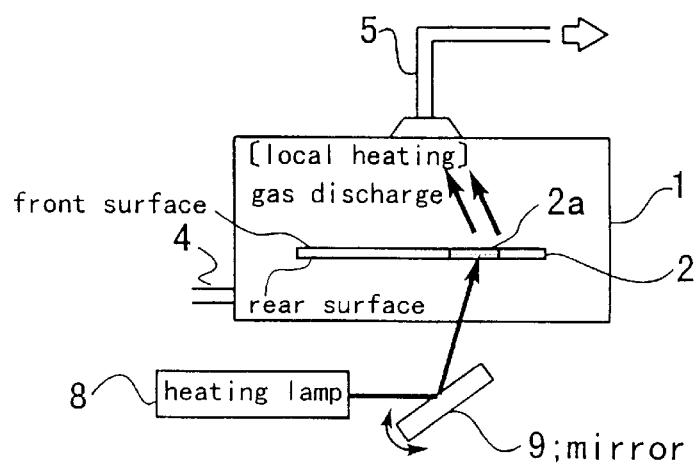
FIG. 2 is a diagram showing a configuration of an organic substance analyzing system in a second embodiment of the present invention for identifying and quantifying organic substances adhering to the surface of a sample such as a wafer.

FIG. 2 is a diagram showing a configuration of an organic substance analyzing system in a second embodiment according to the present invention for identifying and quantifying organic substances adhering to the surface of a sample such as a wafer. In FIG. 2, there are shown a chamber 1, a wafer 2, i.e., a sample, a carrier gas supply pipe 4, and a discharged gas collecting pipe 5, which are the same as those of the organic substance analyzing system shown in FIG. 1. In FIG. 2, a discharged gas collecting means 6 and a discharged gas analyzing means 7 are provided as in the case sown by FIG. 1, however they are not illustrated in FIG. 2.

In FIG. 2, a heating lamp 8 is disposed outside the chamber 1 as a heating light source. A mirror 9 works as an irradiating means for irradiating a heating position of the wafer 2 located in the chamber 1 with a light from the heating lamp 8. The chamber 1 is formed of a light-transmitting material along a path of the light beam passing through from a mirror 9 to the wafer 2.

The heating lamp 8 and an irradiating means (mirror) 9 locally irradiates and heats the back side or rear side of a portion 2a on the surface of the wafer 2 to be analyzed, thus discharging gases from the surface of the wafer 2. The gas containing the organic substances discharged from the wafer 2 is collected and analyzed by a method similar to that employed in the first embodiment and hence the description thereof will be omitted. Thus, the wafer 2 is examined locally for the analysis of organic substances adhering to a local portion of the surface of the wafer 2.

As a heating method other than the above-explained method using the lamp, a laser may be employed instead of the heating lamp 8 to heat the wafer 2. If a laser is employed, the laser light source is disposed outside the chamber 1. A heated position is irradiated with a laser light from this laser light source by an irradiating means from the back side of the wafer 2 disposed in the chamber 1. In this case, too, the chamber 1 is formed of a laser light-transmitting material. Alternatively, a laser light guiding material may be provided through the wall of the chamber 1 so as to radiate the laser light inside the chamber 1.

Another heating method is a method of employing an electron beam irradiation. In this case, an electron beam source is disposed outside the chamber 1, and an electron beam emitted by the electron beam source is launched and radiated at a heated position from the back side of the wafer 2 located in the chamber 1 by an irradiating means. In this case, too, in a path along which the electron beam passes through, the chamber 1 is formed of a electron beam transmitting material.

The apparatus and method described above make it possible to achieve a local analysis of organic substances on the surface of the wafer. Thus, the distribution of the organic substances on the surface of the wafer may be evaluated and analyzed.

Third Embodiment

Figure 3:
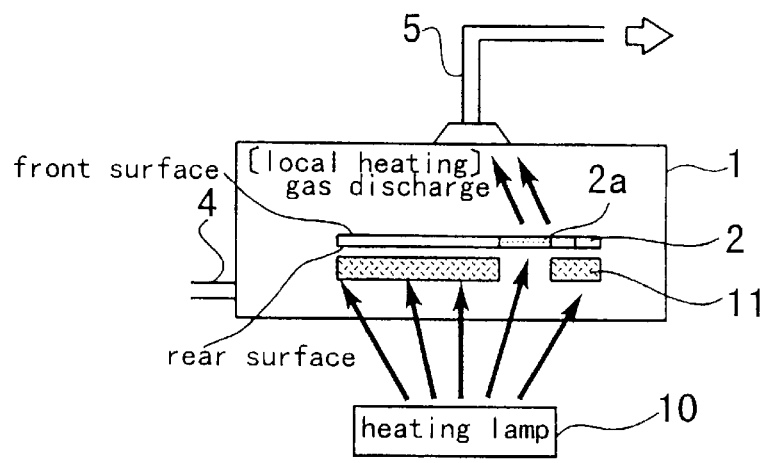
FIG. 3 is a diagram showing a configuration of an organic substance analyzing system according to a third embodiment of the present invention.

FIG. 3 is a diagram showing a configuration of an organic substance analyzing system in a third embodiment according to the present invention for identifying and quantifying organic substances adhering to the surface of a sample such as a wafer. In FIG. 3, there are shown a chamber 1, a wafer 2, i.e., a sample, a carrier gas supply pipe 4, and a discharged gas collecting pipe 5, which are the same as those of the organic substance analyzing system shown in FIG. 1. A discharged gas collecting means 6 and a discharged gas analyzing means 7 included in the organic substance analyzing system are the same as those shown in FIG. 1 and hence not shown in FIG. 3.

A heating lamp 10 as a heating light source is disposed outside the chamber 1. A light-shielding mask 11 causes light rays from the heating lamp 8 to radiate only at a predetermined portion of the wafer 2 placed in the chamber 1. A wide area of a wall of the chamber 1 is formed of a light-transmitting material. Light rays emitted by the heating light source 10 are radiated through the wall of the chamber 1 over a wide area of the light-shielding mask 11. The light-shielding mask 11 is provided with a light-transmitting opening in correspondence with a position to be heated on the wafer 2. Therefore, the light rays from the heating light source 10 are radiated locally on a back side of a portion 2a on the surface of the wafer 2 to be analyzed, thus heating the back side of the portion 2a.

As stated above, by using the heating lamp 10 and the light-shielding mask 11, the back side or rear side of the portion 2a to be analyzed on the surface of the wafer 2 is irradiated locally and heated, and thus gases are discharged from the surface of the wafer 2. The gas containing the organic substances discharged from the wafer 2 is collected and analyzed by a method similar to that employed in the first embodiment, and hence the description thereof will be omitted. Thus, the wafer 2 is examined locally for the analysis of organic substances adhering to a local portion of the surface of the wafer 2.

The apparatus and method described above make it possible to achieve a local analysis of organic substances on the surface of the wafer, thus evaluation of the distribution of the organic substances on the surface of the wafer are performed.

Fourth Embodiment

As described above, in the first to the third embodiments, the wafer having a surface portion to be examined is heated from the back side of the wafer. In contrast, in an organic substance analyzing system in a fourth embodiment according to the present invention, a sample such as a wafer with a surface portion to be examined is heated directly from the surface side thereof.

Figure 5:
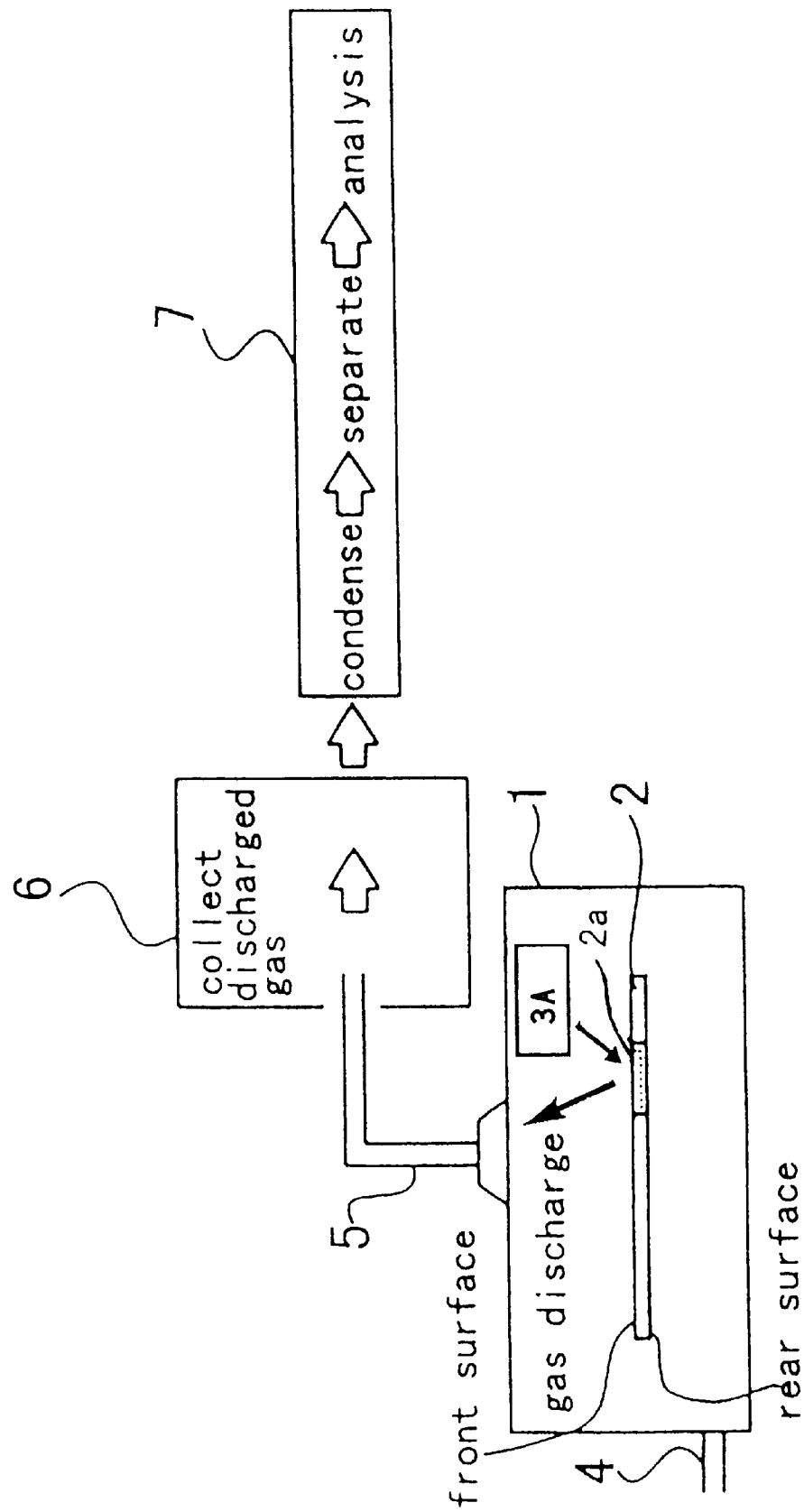
FIG. 5 is a diagram showing a configuration of an organic substance analyzing system according to a fourth embodiment of the present invention.

As shown in FIG. 5, a heating device 3A, such as the irradiating light or the electron beam of the apparatus shown in FIG. 2 or 3, may be irradiated on the surface of the wafer 2 from the surface side thereof. The light emitted by the heating lamp, the laser beam emitted by the laser, or the electron beam mentioned in the description of the first to the third embodiments may be used in this way.

In the fourth embodiment, a heating lamp, a laser light source or an electron beam source, and an irradiating means for guiding light rays or an electron beam may be arranged and configured properly. Thus, the portion 2a on the surface of a wafer to be examined may be heated locally and directly from the surface side thereof, and gases are discharged therefrom.

Accordingly, the portion 2a may be heated efficiently. Therefore, the temperature distribution on the wafer becomes steeper as compared with the temperature distribution in the case when the wafer is heated from the back side thereof. Thus, gases may be discharged only from a desired portion to be examined.

By the apparatus and method described above, it is possible to achieve a local analysis of organic substances on the surface of the wafer. Thus, evaluation of the distribution of the organic substances on the surface of the wafer may be performed.

Fifth Embodiment

An organic substance analyzing system in a fifth embodiment according to the present invention to examine a wafer locally for organic substance analysis is similar to those in the first to the fourth embodiments, except that the system in the fifth embodiment is additionally provided with a temperature rise suppressing means for suppressing temperature rise in portions on the surface of a wafer other than a portion to be examined by cooling the wafer from the back side thereof. Regions of the surface on the wafer other than the portion to be examined can be kept at relatively low temperatures to suppress the discharging of gases from the regions which need not be examined. Thus, gases may be discharged only from the desired portion to be examined. Consequently, organic substances adhering to the surface of the wafer can be more accurately analyzed and evaluated.

It is desirable to cool the wafer from the back side thereof so as to cool regions other than the portion to be examined, particularly, to cool a peripheral region around the portion to be examined to suppress temperature rise.

Figure 6:
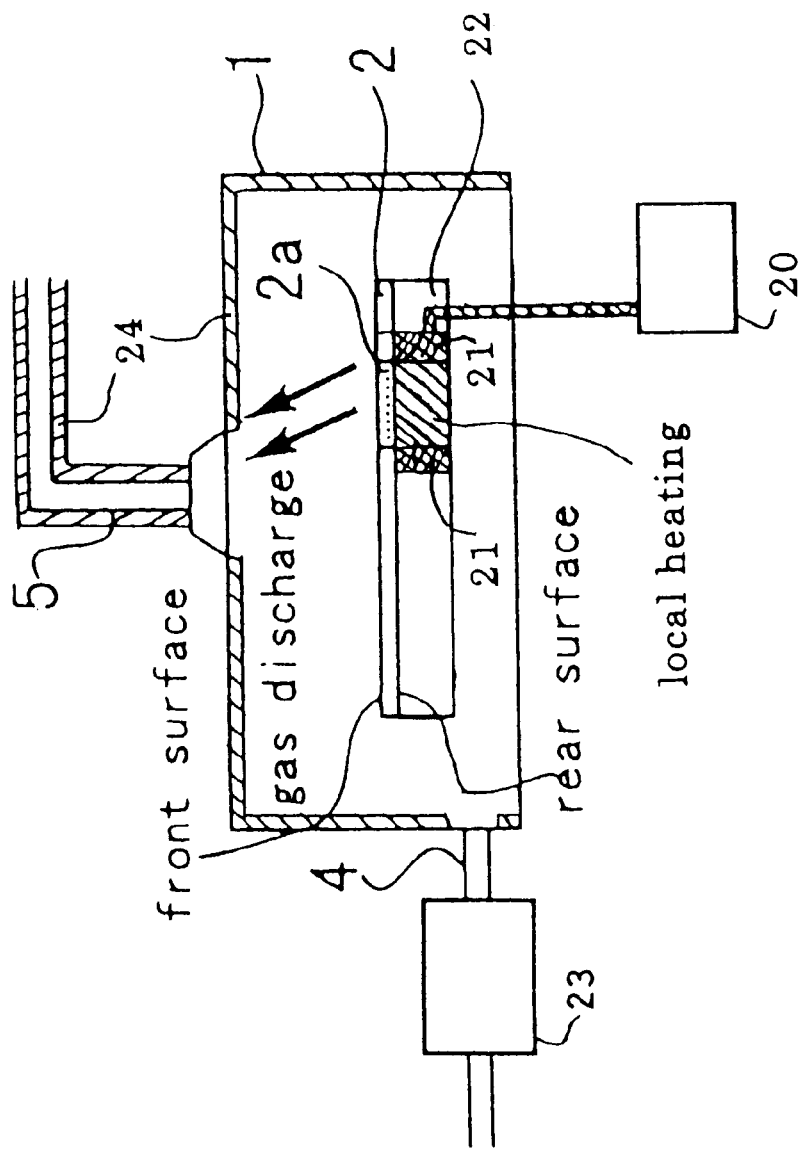
FIG. 6 is a diagram showing a configuration of an organic substance analyzing system according to a fifth embodiment of the present invention.
Figure 7:
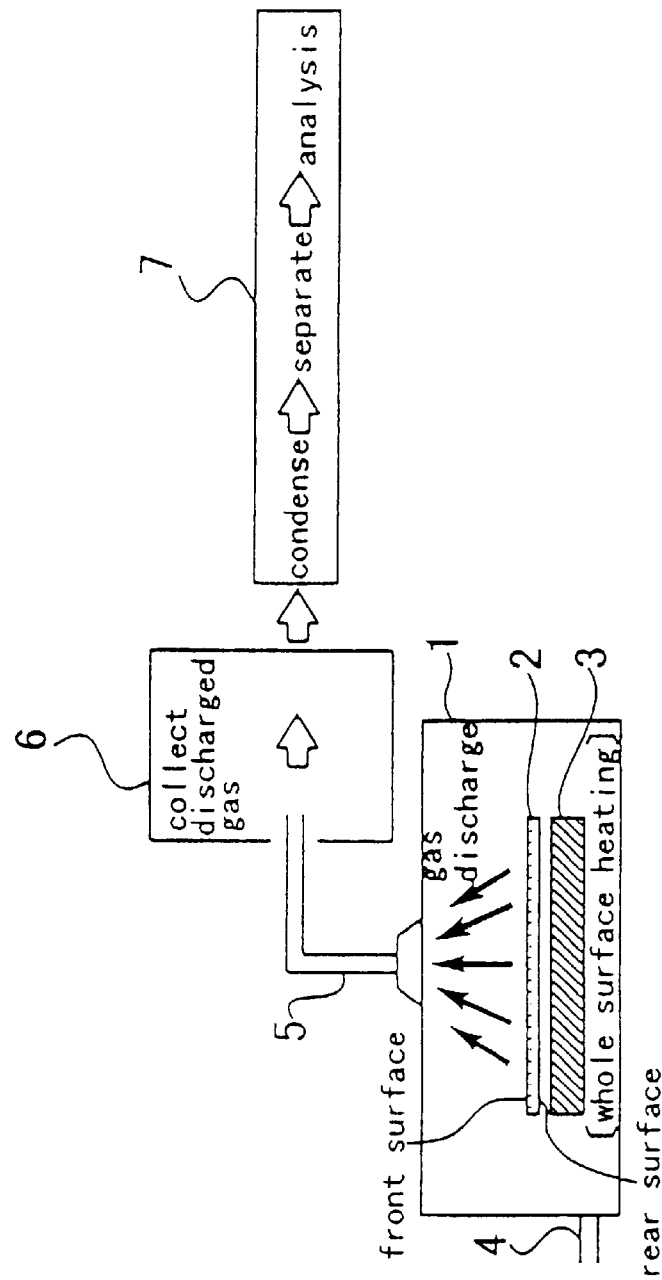
FIG. 7 is a diagram showing a conventional configuration of an organic substance analyzing system using a GC/MS measuring method.

As shown in FIG. 6, a concrete example of a means for cooling the wafer from the back side thereof is a water-cooling means which cools regions other than the portion to be examined 2a by a cooling water. The cooling water supply device 20 has a cooling water passage formed 21 in a supporting means 22 for wafers. Thereby, gases are discharge accurately only from the desired portion to be examined 2a.

Another means for cooling the wafer from the back side thereof is, for example, a carrier gas temperature regulating means 23 which supplies a carrier gas of a relatively low temperature.

The water-cooling means and the carrier gas temperature regulating means may be used in combination for cooling with an improved cooling efficiency.

The fifth embodiment is provided with an additional means 24 to heat the gas collecting pipe 5 and the inner surface of the wall of the chamber 1 to maintain the temperature of the gas collecting pipe 5 and the inner surface of the wall of the chamber 1 at a predetermined level.

If a carrier gas of a relatively low temperature is used, the temperatures of the gas collecting pipe 5 and the inner surface of the wall of the chamber 1 become relatively low, and the organic substances contained in the gases discharged out of the wafer may be adsorbed by the gas collecting pipe 5 and the inner surfaces of the wall of the chamber 1 and may not be collected effectively. However, this can be prevented by heating the gas collecting pipe 5 and the inner surface of the wall of the chamber 1.

By the apparatus and method described above, a local analysis of organic substances on the surface of the wafer may be performed effectively, and the distribution of the organic substances on the surface of the wafer are evaluated accurately.

Sixth Embodiment

Figure 4:
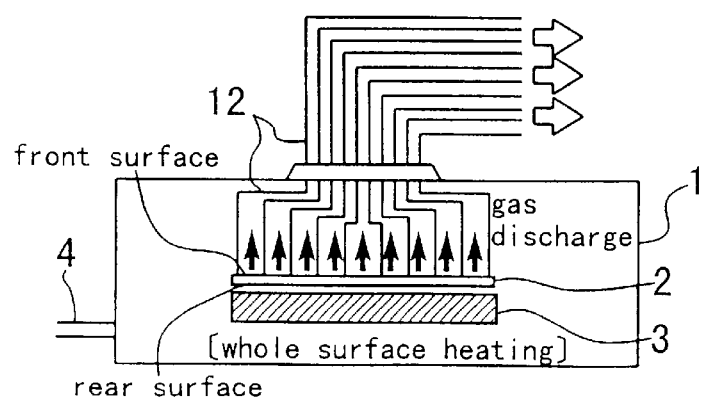
FIG. 4 is a diagram showing a configuration of an organic substance analyzing system according to a sixth embodiment of the present invention.

FIG. 4 is a diagram showing a configuration of an organic substance analyzing system in a sixth embodiment according to the present invention for identifying and quantifying organic substances adhering to the surface of a sample such as a wafer.

In FIG. 4, there are shown a chamber 1, a wafer 2, i.e., a sample (object of analysis) placed in the chamber 1, a heating means 3 (a heater and so on) for heating the wafer 2 and a carrier gas supply pipe 4. These components are the same as those shown in FIG. 1. A discharged gas collecting means 6 and a discharged gas analyzing means 7 included in the organic substance analyzing system are the same as those shown in FIG. 1 and hence not shown in FIG. 4.

Discharged gas collecting pipes 12 separate a region on the surface of the wafer 1 to collect the discharged gases from the wafer 1 for every portion section. The gas collecting pipes 12 are extended from outside the chamber 1 through a wall of the chamber 1 respectively to positions close to the surface of the wafer 2 placed in the chamber 1. The inner ends at which the gas collecting pipes 12 face the wafer 2 are disposed close to the surface of the wafer 2 in order that gases discharged from different sections of the surface of the wafer 2 may not mix.

The gas collecting means (see FIG. 1) collects the discharged gases for every section on the wafer 2 separately, and the discharged gases collected are analyzed for every section by a discharged gas analyzing means (see FIG. 1).

A heating means 10 included in this organic substance analyzing system heats the entire back surface of the wafer 2 to discharge gases out of the surface of the wafer 2, and the discharged gases can be collected and analyzed separately for the local organic substance analysis.

In a modification of the sixth embodiment, both the local heating of the wafer as mentioned in the description of the first to the third embodiments and the collection of discharged gases from the separate sections on the surface of the wafer may be simultaneously carried out.

Thus, the wafer is heated locally to discharge gases from the wafer surface, and at the same time the gases can be collected separately from the adjacent sections without mixing the gases discharged from the adjacent regions. This makes it possible to perform the local organic substance analysis for analyzing organic substances adhering to the surface of the wafer more precisely and with a higher accuracy.

As is apparent from the foregoing descriptions for each embodiments of the present invention, in the organic substance analyzing system for identifying and quantifying organic substances adhering to the surface of a sample such as a semiconductor wafer, a local analysis of organic substances on the surface of the sample is performed with a high accuracy. Further, the distribution of the organic substances on the surface of the wafer may be evaluated and analyzed.

Obviously many modifications and variations of the present invention are possible in the light of the above teachings. It is therefore to be understood that within the scope of the appended claims the invention may by practiced otherwise than as specifically described.

What is claimed is:

1. An organic substance analyzing system for identifying and quantifying organic substances adhering to a surface of a sample, comprising:
    a chamber for holding the sample;
    a heating means for heating only a portion to be analyzed of the surface of the sample, the portion to be analyzed having an area smaller than an area of the surface of the sample, the heating means heating the portion to be analyzed from the back side of the sample;
    a discharged gas collecting means connected to said chamber for collecting gases discharged out of the surface of said sample; and
    a discharged gas analyzing means for analyzing said discharged gases collected by said discharged gas collecting means.

2. The organic substance analyzing system according to claim 1, wherein said heating means comprises a heating light source, and an irradiating means for locally irradiating the back side of said portion to be analyzed with a light emitted by said heating light source.

3. The organic substance analyzing system according to claim 1, wherein said heating means comprises a laser light source, and an irradiating means for locally irradiating the back side of said portion to be analyzed with a laser light emitted by said laser light source.

4. The organic substance analyzing system according to claim 1, wherein said heating means comprises an electron beam irradiating source, and an irradiating means for locally irradiating the back side of said portion to be analyzed with an electron beam emitted by said electron beam irradiating source.

5. The organic substance analyzing system according to claim 1, wherein said heating means comprises:
    a light-shielding mask disposed on the back side of the sample and provided with a light-transmitting opening at a position corresponding to a portion of said sample to be analyzed,
    a heating light source, and
    an irradiating means for irradiating said light-shielding mask with a light emitted from said heating light source.

6. The organic substance analyzing system according to claim 1, further comprising a cooling means for cooling the back side of said sample to suppress a temperature rise in regions except for said portion to be analyzed.

7. The organic substance analyzing system according to claim 6, wherein said cooling means includes a cooling water supply means for cooling said back side of said sample with a cooling water.

8. The organic substance analyzing system according to claim 6, wherein said cooling means includes a temperature regulating means for lowering a temperature of a carrier gas to be supplied to said chamber.

9. The organic substance analyzing system according to claim 6, wherein said discharged gas collecting means comprises a collecting pipe, further comprising a heating means for heating said chamber and said collecting pipe as to maintain the temperatures thereof at a desired level.

10. The organic substance analyzing system according to claim 1, wherein said discharged gas collecting means separately collects gases from each of a plurality of the portions to be analyzed, and said discharged gas analyzing means analyzes said discharged gases collected for each of the portions to be analyzed separately.

11. An organic substance analyzing system for identifying and quantifying organic substances adhering to the surface of a sample, comprising:
    a chamber for holding the sample;
    a heating means for heating only a portion to be analyzed of the surface of the sample, the portion to be analyzed having an area smaller than an area of the surface of the sample, the heating means heating the portion to be analyzed from the front side of said sample; and
    a discharged gas collecting means connected with said chamber for collecting gases discharged out of said sample;
    an analyzing means for analyzing said discharged gases collected by said discharged gas collecting means; and
    cooling means for cooling the back side of the sample to suppress a temperature rise in regions except for the portion to be analyzed.

12. The organic substance analyzing system according to claim 11, wherein said heating means comprises a heating light source, and an irradiating means for locally irradiating said portion to be analyzed on said sample surface with a light emitted by said heating light source.

13. The organic substance analyzing system according to claim 11, wherein said heating means comprises a laser light source, and an irradiating means for locally irradiating said portion to be analyzed on said sample surface with a laser light emitted by said laser light source.

14. The organic substance analyzing system according to claim 11, wherein said heating means comprises an electron beam irradiating source, and an irradiating means for locally irradiating said portion to be analyzed on said sample surface with an electron beam emitted by said electron beam irradiating source.

15. An organic substance analyzing system for identifying and quantifying organic substances adhering to each of a plurality of portions of the surface of a sample, comprising:

a heating means for heating said sample placed in a chamber;

a discharged gas collecting means for simultaneously collecting gases discharged out of each of the portions of said sample without substantially mixing the gases discharged from the plurality of portions of the sample; and a discharged gas analyzing means for analyzing said gases collected by said discharged gas collecting means for each of the portions separately.

* * * * *